United States Patent
Abdur-Rashid et al.

(10) Patent No.: US 7,256,311 B2
(45) Date of Patent: Aug. 14, 2007

(54) PROCESS FOR HYDROGENATING UNACTIVATED IMINES USING RUTHENIUM COMPLEXES AS CATALYSTS

(76) Inventors: Kamaluddin Abdur-Rashid, 3816 Morning Star Drive, Mississauga, Ontario (CA) L4T 1Y9; Robert H. Morris, 114 Browning Avenue, Toronto, Ontario (CA) M4K 1W3

( * ) Notice: Subject to any disclaimer, the term of this patent is extended or adjusted under 35 U.S.C. 154(b) by 116 days.

(21) Appl. No.: 10/513,321

(22) PCT Filed: May 15, 2003

(86) PCT No.: PCT/CA03/00689

§ 371 (c)(1),
(2), (4) Date: Jun. 1, 2005

(87) PCT Pub. No.: WO03/097571

PCT Pub. Date: Nov. 27, 2003

(65) Prior Publication Data

US 2005/0209487 A1  Sep. 22, 2005

Related U.S. Application Data

(60) Provisional application No. 60/380,256, filed on May 15, 2002.

(51) Int. Cl.
*C07C 209/52* (2006.01)
(52) U.S. Cl. .................. 564/415; 564/489
(58) Field of Classification Search .............. None
See application file for complete search history.

(56) References Cited

FOREIGN PATENT DOCUMENTS

WO    WO02/08169    1/2002

OTHER PUBLICATIONS

Abdur-Rashid et al., Organometallics (2001), 20, p. 1047-1049.*
Abdur-Rashid, K. et al., "RuHCl(diphosphine)(diamine): Catalyst Precursors for the Steroselective Hydrogenation of Ketones and Imines", Organometallics, 2001, pp. 1047-1049, vol. 20.

Cobley, C. J. et al., "Enantioselective Hydrogenation of Imines using a Diverse Library of Ruthenium Dichloride (diphosphine) (diamine) Precatalysts", Advanced Synthesis and Catalysis, 2003, pp. 195-201, vol. 345.

Henschke, J. P. et al., "Synthesis and Application of HexaPHEMP, a Novel Biaryl DiPhosphine Ligand", Advanced Synthesis and Catalysis, 2003, pp. 300-307, vol. 345.

Cobley, C. J. et al., "The synthesis of S 18986, a chiral AMPA receptor modulator, via catalytic asymmetric hydrogenation", Tetrahedron: Asymmetry, 2003, pp. 3431-3433, vol. 14.

* cited by examiner

*Primary Examiner*—Brian Davis
(74) *Attorney, Agent, or Firm*—Bereskin & Parr; Patricia Folkins

(57) ABSTRACT

A process is provided for the hydrogenation or asymmetric hydrogenation of dialkyl, alkylalkenyl and dialkenyl imines of formula (II) to provide amines of formula (III), wherein, (i) $R^1$ and $R^2$ are optionally substituted cyclic, linear or branched alkyl or alkenyl; $R^3$ is a hydrogen atom, a hydroxy radical, optionally substituted $C_1$ to $C_8$ cyclic, linear or branched alkyl or alkenyl, optionally substituted aryl; or (ii) $R^1$ is alkyl or alkenyl, $R^2$ is alkyl or alkenyl and the two are linked together or with $R^3$ to form one or more rings; using a catalytic system comprising a base and a ruthenium complex containing (1) a diamine and (2) a diphosphine ligand or monodentate phosphine ligands in hydrogenation and asymmetric hydrogenation processes

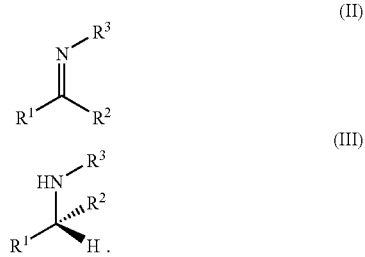

25 Claims, No Drawings

PROCESS FOR HYDROGENATING UNACTIVATED IMINES USING RUTHENIUM COMPLEXES AS CATALYSTS

FIELD OF THE INVENTION

The present invention relates to the field of catalytic hydrogenations, using $H_2$, and more particularly to the use of a catalytic system comprising a base and a ruthenium complex containing (1) a diamine and (2) a diphosphine ligand or monodentate phosphine ligands, in hydrogenation, including asymmetric hydrogenation processes, for the reduction of unactivated imines.

BACKGROUND OF THE INVENTION

Although many highly enantioselective chiral catalysts and catalytic processes are available for the asymmetric hydrogenation and transfer hydrogenation of C=C and C=O bonds, relatively few exist for effective reduction of the analogous C=N function. The production of chiral amines via this methodology still represents a major challenge. Over the past decade, there has been significant and steady progress in this field with the preparation of catalysts based on complexes of rhodium, iridium, ruthenium and titanium.

In 1997 B. R. James reviewed the preparation of chiral amines by homogeneous catalytic hydrogenation reactions involving metal complexes (James, *Catalysis Today* 1997, 37, 209-221). The review by James names several other systems based on rhodium for the asymmetric hydrogenation of imines but they suffer from drawbacks. Either the enantioselectivity is low or the conditions are severe. In a recent U.S. patent, X. Zhang et al. describe the use of BICP, a chiral diphosphine ligand, on rhodium and iridium in the asymmetric hydrogenation of internal C=N bonds at 1000 psi $H_2$ at room temperature to produce amines with enantiomeric excesses (e.e.) ranging from 65 to 94%. (X. Zhang, U.S. Pat. No. 6,037,500, 2000). Spindler and co-workers demonstrated the use of in situ generated iridium JOSIPHOS complexes for the enantioselective hydrogenation of imines (Spindler et al., *Angew. Chem., Int. Ed Engl.*, 1990, 29, 558; Blaser and Spindler, *Topics in Catalysis*, 1997, 4, 275). This process was subsequently modified and applied to the industrial production of the imine precursor to (S)-Metolachlor, a valuable agrichemical product, then for Ciba-Giegy, now for Novartis. The production of S-Metolachlor is an example of a large-scale industrial process that depends on the homogenous hydrogenation of a prochiral imine.

Noyori and coworkers have described an efficient catalyst system generated from the complex Ru($\eta^6$-arene)(tosyldiamine)Cl for the asymmetric hydrogenation of imines by transferring hydrogen from triethylammonium formate (Noyori et al., *Acc. Chem. Res.* 1997, 30, 97-102). This is the first really effective imine reduction system based on ruthenium although other straight hydrogenation systems with much lower activity and selectivity have been reported as reviewed by James (supra).

Buchwald and co-workers prepared and effectively employed various chiral ansa-titanocene complexes for both hydrogenation and hydrosilylation of imines (Willoughby and Buchwald, *J. Am. Chem. Soc.*, 1992, 114, 7562; *J. Am. Chem. Soc.*, 1994, 116, 8952 and 11703). The need to activate the catalyst by the addition of butyl-lithium and phenyl silane limits the scope and applicability of this process. This system also suffers from the drawback of being very oxygen and water sensitive.

A recent article by Kobayashi and Ishitani on catalytic enantioselective addition to imines also provides a comprehensive review on other advances in enantioselective hydrogenation of imines (Kobayashi and Ishitani, *Chem. Rev.*, 1999, 99, 1069). These include the use of chiral iridium diphosphine complexes of the type [Ir(P—P)HI$_2$]$_2$ (where P—P represents a chiral diphosphine ligand) reported by Osborn and co-workers (Chan et al., *J. Am. Chem. Soc.*, 1990, 112, 9400; Sablong et al., *Tetrahedron Lett.*, 1996, 37, 4937). These systems were reasonably active, however, the enantioselectivities were only moderate. Zhang and co-workers reported the synthesis of a new class of chiral iridium binaphane complexes (Xiao and Zhang, *Angew. Chem. Int. Ed. Engl.*, 2001, 40, 3425) and their use for the asymmetric hydrogenation of imines. More recently Rautenstrauch et al. (WO 02/22526) reported the use of metal complexes with P—N bidentate ligands in the catalytic hydrogenation of carbon-heteroatom double bonds, including C=N double bonds.

Despite the successes of some of these catalytic hydrogenation processes, there are certain significant drawbacks. These include high operating pressures (typically >50 bar $H_2$), high catalyst loading and the use of expensive iridiun- and rhodium-based systems. Most of these processes are specific for only certain types of substrates or a group of closely related substrates. In addition, activity and enantioselectivity also tends to be highly substrate dependent, which in some cases necessitates the development of an entire catalytic system and process for only one substrate or a very closely related group of substrates.

Hence, there remains the need to identify a general class of structurally related catalysts that are chemically robust and give high activity and enantioselectivity in the asymmetric hydrogenation of a broad range of imine substrates. It is particularly desirable to have a class of modular catalysts whereby one can readily vary individual parts of the catalyst, especially the chiral ligand, so that the best match of substrate and catalyst can be identified by rapid through-put combinatorial screening.

Noyori and co-workers have pioneered the use of ruthenium complexes bearing a chelating diphosphine ligand (or two monodentate phosphines) and a chelating diamine ligand for the catalytic asymmetric hydrogenation of ketones. At least one and usually both of the chelating ligands are chiral. The various papers and patents of Noyori et al. have demonstrated the highly efficient reduction of various functionalised and unfunctionalised ketones using this class of catalysts. It was also demonstrated by Noyori and co-workers (Ohkuma et al., *J. Am. Chem. Soc.*, 1995, 107, 2675 and 10417) that a fully isolated and characterised ruthenium(II)diphosphinediamine complex could be used as catalyst. High activity and high selectivity were generally associated with the use of chiral biaryl-phosphines (eg. Tol-BINAP and Xyl-BINAP) and diamines (eg. DPEN and DAIPEN).

It was demonstrated for the first time by Abdur-Rashid et al. that similar classes of Noyori-type ruthenium(II)(phosphine)₂(diamine) complexes (Abdur-Rashid et al., *Organometallics*, 2000, 20, 1655) or ruthenium(II)diphosphinediamine complexes (Abdur-Rashid et al., Oral and Poster Presentations at the Canadian Society for Chemistry 83$^{rd}$ Conference and Exhibition (Calgary, Alberta), May 2000) could catalyse the hydrogenation and asymmetric hydrogenation of activated (aromatic) imines. Since these publications, Chirotech Technology Limited filed a patent (WO 02/08169 A1) for an imine hydrogenation process, based on a similar class of complexes for the hydrogenation and asymmetric hydrogenation of activated (aromatic) imines. The work presented by Abdur-Rashid et al. at the May 2000 CSC meeting in Calgary was subsequently published in 2001 (*Organometallics*, 2001, 20, 1047).

The imine hydrogenation work of Abdur-Rashid et al. and the patent of Chirotech Technology Limited relates to the use of Noyori-type ruthenium(II)-(phosphine)₂(diamine) and ruthenium(II)diphosphinediamine complexes as catalysts for the reduction of activated imines in which the imine functional group is adjacent to an aromatic aryl ring as illustrated in (I) below.

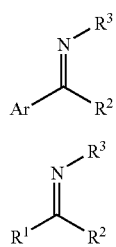

To date, there are no reports in the mainstream or patent literature of the use of such Noyori-type ruthenium(II) complexes for the hydrogenation and asymmetric hydrogenation of unactivated dialkyl, alkylalkenyl or dialkenyl imines as illustrated in (II), where $R^1$ and $R^2$ represents alkyl, alkylalkenyl or dialkenyl substituents. These imines are inherently more difficult to reduce than their activated (aromatic) analogues, and there are only a few reported attempts in the published and patent literature for the catalytic hydrogenation and asymmetric hydrogenation of such compounds.

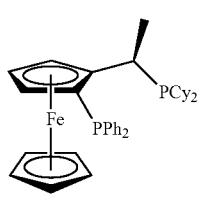

JOSIPHOS

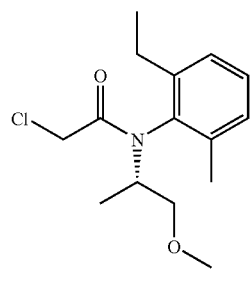

S-Metolachlor

The industrial production of the chiral amine precursor to the potent herbicide S-Metolachor using an iridium-JOSIPHOS catalyst is an example of a successful process that relies on the asymmetric hydrogenation of a dialkyl imine (Togni, *Angew. Chem, Int. Ed Engl.*, 1996, 35, 1475).

There remains a need for efficient catalysts for the hydrogenation and asymmetric hydrogenation of unactivated imines.

SUMMARY OF THE INVENTION

The present inventors have surprisingly found that reduction or hydrogenation of the carbon-nitrogen double bond (C=N) of dialkyl, alkylalkenyl and dialkenyl imine compounds (II) to the corresponding amines (III) can be efficiently carried out using molecular hydrogen ($H_2$), a base and a catalytic system comprising a ruthenium complex bearing (1) a diphosphine ligand or two monodentate phosphine ligands and (2) a diamine ligand. Such processes can also be used to achieve the asymmetric reduction/hydrogenation of prochiral dialkyl, alkylalkenyl or dialkenyl imines to the corresponding chiral amines by using chiral ruthenium complexes bearing chiral diphosphines or chiral monodentate phosphines and/or chiral diamines.

Accordingly, the present invention relates to a process for the hydrogenation and/or asymmetric hydrogenation of dialkyl, alkylalkenyl or dialkenyl imines of formula II to amines of formula III:

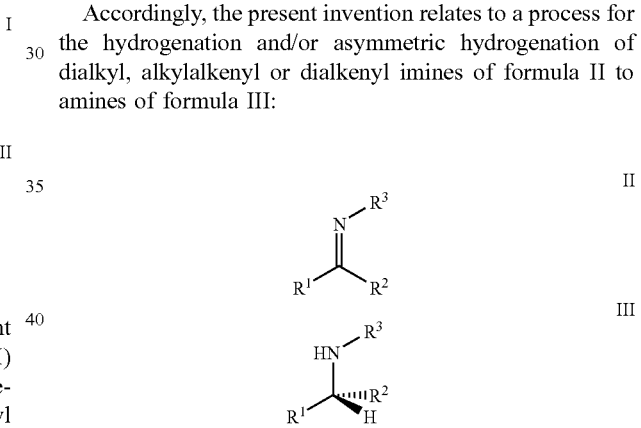

wherein $R^1$ and $R^2$ are independently selected from the group consisting of optionally substituted cyclic, linear and branched alkyl and alkenyl and wherein $R^1$ and $R^2$ may also be linked together, or with $R^3$, to form one or more rings; and $R^3$ is selected from the group consisting of hydrogen, hydroxy, optionally substituted $C_1$ to $C_8$ cyclic, linear and branched alkyl and alkenyl, and optionally substituted aryl;

said process comprising the steps of reacting imines of formula II in the presence of $H_2$ and a catalytic system comprising a base and a ruthenium complex containing (1) a diamine and (2) a diphosphine ligand or monodentate phosphine ligands.

In an embodiment, the present invention relates to a process for preparing enantiomerically enriched chiral dialkyl, alkylalkenyl or dialkenyl amines of formula III, or the opposite enantiomer thereof, from an imine of formula II:

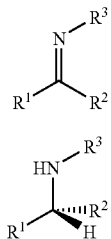

wherein
R¹ and R² are independently selected from the group consisting of optionally substituted cyclic, linear and branched alkyl and alkenyl and wherein R¹ and R² may also be linked together, or with R³, to form one or more rings; and
R³ is selected from the group consisting of hydrogen, hydroxy, optionally substituted $C_1$ to $C_8$ cyclic, linear and branched alkyl and alkenyl, and optionally substituted aryl;
said process comprising the steps of reacting imines of formula II in the presence of $H_2$ and a catalytic system comprising a base and a ruthenium complex containing (1) a diamine and (2) a chiral diphosphine ligand or chiral monodentate phosphine ligands. Optionally, the diamine may also be chiral.

The process involves the catalytic hydrogenation or asymmetric hydrogenation of the corresponding dl, alkylalkenyl or dialkenyl imine, II, in the presence of a base using an achiral or chiral ruthenium complex containing (1) a diamine ligand and (2) an achiral or chiral diphosphine ligand or achiral or chiral monodentate phosphine ligands. In embodiments of the present invention, said ruthenium complexes may have the general formula $RuXY(PR_3)_2(NH_2-Z-NH_2)$ (IV) or $RuXY(R_2P-Q-PR_2)(NH_2-Z-NH_2)$ (V), wherein Z and Q represent chiral or achiral linkers, the ancillary ligands, $PR_3$ and $R_2P-Q-PR_2$, represent monodentate and bidentate phosphines, respectively, and the ligands X and Y represent any anionic ligand such as Cl, Br, I, H, hydroxy, alkoxy or acyloxy. In further embodiments of the present invention, the diamine ligand may have the general formula D—Z—NHR (X), wherein D is an amido donor group.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

DETAILED DESCRIPTION OF THE INVENTION

The present inventors have surprisingly found that unreactive alkyl- and alkenyl-substituted imines, which are notoriously recalcitrant to undergo hydrogenation under milder hydrogenation conditions, may be efficiently hydrogenated, as well as asymmetrically hydrogenated, in the presence of $H_2$ and Noyori-type ruthenium(II) complexes.

Therefore, the present invention relates to a process for the hydrogenation and/or asymmetric hydrogenation of dialkyl, alkylalkenyl or dialkenyl imines of formula II to amines of formula III:

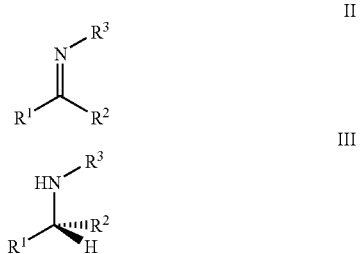

wherein
R¹ and R² are independently selected from the group consisting of optionally substituted cyclic, linear and branched alkyl and alkenyl and wherein R¹ and R² may also be linked together, or with R³, to form one or more rings; and
R³ is selected from the group consisting of hydrogen, hydroxy, optionally substituted $C_1$ to $C_8$ cyclic, linear and branched alkyl and alkenyl, and optionally substituted aryl;
said process comprising the steps of reacting imines of formula II in the presence of $H_2$ and a catalytic system comprising a base and a ruthenium complex containing (1) a diamine and (2) a diphosphine ligand or monodentate phosphine ligands.

In an embodiment, the present invention relates to a process for preparing enantiomerically enriched chiral dialkyl, alkylalkenyl or dialkenyl amines of formula III, or the opposite enantiomer thereof, from an imine of formula II:

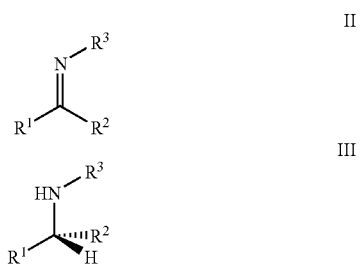

wherein
R¹ and R² are independently selected from the group consisting of optionally substituted cyclic, linear and branched alkyl and alkenyl and wherein R¹ and R² may also be linked together, or with R³, to form one or more rings; and
R³ is selected from the group consisting of hydrogen, hydroxy, optionally substituted $C_1$ to $C_8$ cyclic, linear and branched alkyl and alkenyl, and optionally substituted aryl;
said process comprising the steps of reacting imines of formula II in the presence of $H_2$ and a catalytic system comprising a base and a ruthenium complex containing (1) a diamine and (2) a chiral diphosphine ligand or chiral monodentate phosphine ligands. Optionally, the diamine may also be chiral.

In embodiments of the invention, said ruthenium complexes have the general formula $RuXY(PR_3)_2(NH_2—Z—NH_2)$ (IV) or $RuXY(R_2P—Q—PR_2)(NH_2—Z—NH_2)$ (V), wherein Z and Q represent chiral or achiral linkers, the ancillary ligands, $PR_3$ and $R_2P—Q—PR_2$, represent chiral or achiral monodentate and bidentate phosphines, respectively and the ligands X and Y represent any anionic ligand such as Cl, Br, I, H, hydroxy, alkoxy or acyloxy. These complexes, following activation with a base, catalyse the hydrogenation process.

The ligand $PR_3$ (VI):

(VI)

$PR_3$ represents a chiral or achiral monodentate phosphine ligand wherein each R, taken separately, is independently selected from the group consisting of optionally substituted linear and branched alkyl and alkenyl containing 1 to 8 carbon atoms, optionally substituted cycloalkyl, optionally substituted aryl, or OR and $NR_2$, wherein R is as previously defined; or two R groups bonded to the same P atom are bonded together to form an optionally substituted saturated or aromatic ring having 5 to 8 atoms including the phosphorous atom to which said R groups are bonded.

The ligand $R_2P—Q—PR_2$ (VII):

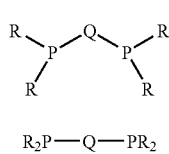

(VII)

$R_2P—Q—PR_2$ represents a chiral or achiral bidentate ligand wherein each R, taken separately, is independently selected from the group consisting of optionally substituted linear and branched alkyl and alkenyl containing 1 to 8 carbon atoms, optionally substituted cycloalkyl, optionally substituted aryl, or OR and $NR_2$, wherein R is as previously defined; or two R groups bonded to the same P atom are bonded together to form an optionally substituted saturated or aromatic ring having 5 to 8 atoms including the phosphorous atom to which said R groups are bonded; Q is selected from the group consisting of optionally substituted linear and cyclic $C_2$-$C_7$ alkylene, optionally substituted metallocenediyl and optionally substituted $C_6$-$C_{22}$ arylene.

In preferred embodiments of this invention, the diphosphine ligand is chiral and includes atropisomeric bis-tertiary phosphines, in which the two phosphorus atoms are linked by a biaryl backbone. Representative members of this class of atropisomeric compounds include BINAP, BIPHEP and BIPHEMP.

In another embodiment of this invention, the diphosphine ligand is a chiral or achiral ligand of the formula $R_2P—NR'—Z—NR'—PR_2$ (VIII):

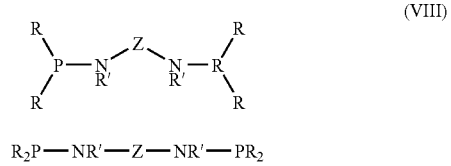

(VIII)

$R_2P—NR'—Z—NR'—PR_2$ wherein each R, taken separately, is independently selected from the group consisting of optionally substituted linear and branched alkyl and alkenyl containing 1 to 8 carbon atoms, optionally substituted cycloalkyl, optionally substituted aryl, or OR and $NR_2$, wherein R is as previously defined; or two R groups bonded to the same P atom are bonded together to form an optionally substituted saturated or aromatic ring having 5 to 8 atoms including the phosphorous atom to which said R groups are bonded; each R', taken separately, is independently selected from the group consisting of hydrogen, optionally substituted linear and branched alkyl or alkenyl containing 1 to 8 carbon atoms, optionally substituted cycloalkyl and optionally substituted aryl; Z is selected from the group consisting of optionally substituted linear and cyclic $C_2$-$C_7$ alkylene, optionally substituted metallocenediyl and optionally substituted $C_6$-$C_{22}$ arylene.

In further embodiments of the invention, the diamine ligand has the formula $NH_2—Z—NH_2$ (IX):

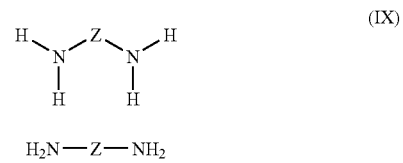

(IX)

$H_2N—Z—NH_2$ wherein Z is selected from the group consisting of optionally substituted linear and cyclic $C_2$-$C_7$ alkylene, optionally substituted metallocenediyl and optionally substituted $C_6$-$C_{22}$ arylene. In preferred embodiments of the present invention, the diamine ligand is chiral and includes (1) compounds in which at least one of the amine-bearing centers is stereogenic, (2) compounds in which both of the amine-bearing centers are stereogenic and (3) atropisomeric bis-tertiary diamines, in which the two nitrogen atoms are linked by a biaryl backbone.

In another embodiment of the present invention, the coordinated amine ligand is a bidentate ligand of the type D—Z—$NHR^4$ (X), which is preferably chiral, wherein Z is selected from the group consisting of optionally substituted linear and cyclic $C_2$-$C_7$ alkylene, optionally substituted metallocenediyl and optionally substituted $C_6$-$C_{22}$ arylene. Preferably, D is an amido group donor, $NR^5$, thus providing an amidoamino ligand, $R^5N—Z—NHR^4$ (XI) that contains an amido group donor $NR^5$ and an amino group donor $NHR^4$. The substituent $R^5$ may be selected from the group consisting of $S(O)_2R^6$, $P(O)(R^6)_2$, $C(O)R^6$, $C(O)N(R^6)_2$ and $C(S)N(R^6)_2$ wherein the substituents $R^6$, taken separately, are each independently selected from the group consisting of hydrogen, optionally substituted linear and branched alkyl and alkenyl containing 1 to 8 carbon atoms, optionally substituted cycloalkyl and optionally substituted aryl. In other embodiments, the donor group D represents a chalcogenide radical such as O, S, Se and Te. In preferred embodiments of the present invention, the coordinated amine ligand is chiral and includes (1) compounds in which the amine-bearing center is stereogenic, (2) compounds in which both the donor-bearing (D) and amine-bearing centers are stereogenic (for example the ligand $CH_3C_6H_4SO_3NCHPhCHPhNH_2$).

The term "alkyl" as used herein means a saturated, linear or branched alkyl groups containing from one to ten, preferably one to eight, more preferably one to six carbon atoms and includes methyl, ethyl, propyl, isopropyl, s-butyl, t-butyl, neopentyl and the like. Optionally, one or more, preferably one or two, more preferably one, of the carbon atoms in an alkyl group may be substituted with a heteroatom such as O, S and N.

When $R^1$ and $R^2$ are linked together, or with $R^3$, to form one or more rings, said rings may be contain from three to twelve atoms, preferably three to ten atoms, having a single ring structure or multiple condensed (fused) ring structure. Further in the rings, one or more, preferably one or two, more preferably one, of the carbon atoms may be substituted with a heteroatom such as O, S and N. An example of such a ring structure is 1-aza-bicyclo[2.2.2]oct-3-ylidene.

The term "alkylene" as used herein refer to divalent groups of the corresponding cyclic, linear or branched alkane.

The term "alkenyl" as used herein means an unsaturated, linear or branched alkenyl group containing from two to ten, preferably two to eight, more preferably two to six carbon atoms and includes vinyl, allyl, butenyl and the like and the like. The alkenyl groups may contain any number of double bonds. Preferably the alkenyl group contains one double bond.

The term "aryl" as used herein means an unsaturated aromatic carbocyclic group containing from six to fourteen carbon atoms having a single ring (e.g., phenyl) or multiple condensed (fused) rings (e.g., naphthyl or anthryl). Preferred aryls include phenyl, naphthyl and the like.

The term "cycloalkyl" or "cyclic alkyl" as used herein refers to cyclic alkyl groups of from three to twelve carbon atoms, preferably from three to eight carbon atoms, having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like. Further in these rings, one or more, preferably one or two, more preferably one, of the carbon atoms may be substituted with a heteroatom such as O, S and N.

The term "metallocenediyl" as used herein refers to a bivalent metallocene group, typically having the following structure:

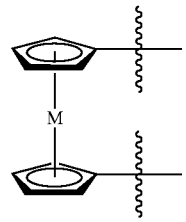

wherein M is a metal, for example iron (Fe).

The term "arylene" as used herein includes biaryldiyl groups and refers to a bivalent group comprising one to three, preferably one to two, aryl groups linked together. Examples of arylene groups include, but are not limited to biphenyldiyl and binaphthyldiyl.

The term "optionally substituted" as used herein means that the corresponding group is either unsubstituted or substituted. When a group is substituted the substituents may include one to five, preferably one to three, more preferably one to two, groups independently selected from alkyl, alkoxy, polyalkyleneglycol, carboxylic esters, OH, halo, cycloalkyl, aryl, and halo-substituted-aryl. As to any of the above groups that contain 1 or more substituents, it is understood, of course, that such groups do not contain any substitution or substitution patterns which are sterically impractical and/or synthetically non-feasible.

The term "halo" as used herein means halogen and includes chloro, flouro, bromo and iodo.

The term "alkoxy" as used herein means saturated, cyclic, linear or branched O-alkyl groups containing from one to ten, preferably one to eight, more preferably one to six carbon atoms and includes methoxy, ethoxy, propoxy, t-butyloxy and the like.

The term "acyloxy" as used herein means saturated, cyclic, linear or branched O-acyl groups containing from one to ten, preferably one to eight, more preferably one to six carbon atoms and includes acetoxy and the like.

The ruthenium catalyst complexes may be prepared, for example, as described by Abdur-Rashid et al. (*Organometallics*, 2001, 21, 1047). Many of the ligands described above are known in the art and, unless specified differently in the Examples, are obtained according to methods known in the art. The ligands that are new can be obtained by modifying known procedures according to the knowledge of a person skilled in the art.

As previously mentioned, the catalytic system characterizing the process of the present invention comprises a base. Said base can be the substrate itself, if the latter is basic, or any conventional base. One can cite, as non-limiting examples, organic non-coordinating bases such as DBU, $NR_3$, phosphazene bases, alkaline or alkaline-earth metal carbonates, carboxylate salts such as sodium or potassium acetate, or alcoholates or hydroxide salts. Preferred bases are the alcoholate or hydroxide salts selected from the group consisting of the compounds of formula $(R^7O)_2M'$ and $R^7OM''$, wherein M' is an alkaline-earth metal, M" is an alkaline metal and $R^7$ is selected from the group consisting of hydrogen and $C_1$ to $C_6$ linear and branched alkyl.

A typical process involves the mixture of the substrate with the ruthenium complex and a base, possibly in the presence of a solvent, and then treating such a mixture with molecular hydrogen at a chosen pressure and temperature.

The complexes can be added to the reaction medium in a large range of concentrations. As non-limiting examples, one can cite a substrate to complex (S/com) ratio of $10^5$ to 20. Preferably, the substrate to complex ratio will be in the range of 10 to 1 respectively. It goes without saying that the optimum concentration of complex will depend on the nature of the latter and on the pressure of $H_2$ used during the process.

Useful quantities of base, added to the reaction mixture, may be comprised in a relatively large range. One can cite, as non-limiting examples, ranges between 1 to 50000 molar equivalents relative to the complex, preferably 10 to 2000. However, it should be noted that it is also possible to add a small amount of base (e.g. base/com=1 to 3) to achieve high hydrogenation yields.

The hydrogenation reaction can be carried out in the presence or absence of a solvent. When a solvent is required or used for practical reasons, then any solvent current in hydrogenation reactions can be used for the purposes of the invention. Non-limiting examples include aromatic solvents such as benzene, toluene or xylene, hydrocarbon solvents such as hexane or cyclohexane, ethers such as tetrahydrofuran, or yet primary or secondary alcohols, or mixtures thereof. A person skilled in the art is well able to select the solvent most convenient in each case to optimize the hydrogenation reaction.

In the hydrogenation process of the invention, the reaction can be carried out at a $H_2$ pressure comprised between $10^5$ Pa and $80 \times 10^5$ Pa (1 to 80 bars). Again, a person skilled in the art is well able to adjust the pressure as a function of the catalyst load and of the dilution of the substrate in the solvent. As examples, one can cite typical pressures of 1 to $40 \times 10^5$ Pa (1 to 40 bar).

The temperature at which the hydrogenation can be carried out is comprised between 0° C. and 100° C., more preferably in the range of between 20° C. and 60° C. Of course, a person skilled in the art is also able to select the preferred temperature as a function of the melting and boiling point of the starting and final products.

Preferably, the process of the present invention provides an effective means of preparing a wide range of chiral amines. It is desirable that the enantiomeric enrichment or excess (ee) of the amine (III) is at least 50% ee, and more preferably at least 80% ee, or higher. If necessary, any shortfall in ee can be subsequently corrected by crystallization techniques known by persons skilled in the art. It is also important to achieve a high conversion of substrate to product, preferably at least 80% conversion, and more preferably at least 90% conversion.

The following non-limiting examples are illustrative of the present invention:

EXAMPLES

Materials and Methods

The invention will now be described in further details by way of the following examples, wherein the temperatures are indicated in degrees centigrade and the abbreviations have the usual meaning in the art. The ligand R,R—DPPACH is a known compound that was previously used in rhodium complexes for the hydrogenation of C=C double bonds (Fioriani et al., *J. Mol. Catal.*, 1979, 5, 303), (Onuma et al., *Bull. Chem. Soc. Jpn.*, 1980, 53, 2012; *Chem Lett.*, 1980, 5, 481).

All the procedures described hereafter have been carried out under an inert atmosphere unless stated otherwise. Hydrogenations were carried out in open glass tubes placed inside a stainless steel autoclave or Schlenk flasks attached to a vacuum line. $H_2$ gas was used as received. All preparations and manipulations were carried out under $H_2$, $N_2$ or Ar atmospheres with the use of standard Schlenk, vacuum line and glove box techniques in dry, oxygen-free solvents. Tetrahydrofuran (THF), diethyl ether ($Et_2O$) and hexanes were dried and distilled from sodium benzophenone ketyl. Deuterated solvents were degassed and dried over activated molecular sieves. Ruthenium trichloride, triphenylphosphine, R,R—DPEN, R,R—CYDN, ketones and amines were purchased from Aldrich. The precursor complex RuHCl($PPh_3$)$_3$ was prepared by a modification of the procedure reported by Schunn et al. (*Inorg. Synthesis*, 1970, 131). The complexes RuHCl(R—BINAP)($PPh_3$), RuHCl(R,R—DPPACH)($PPh_3$), RuHCl(R—BINAP)(R,R—CYDN), RuHCl(R—BINAP)(R,R—DPEN), RuHCl(R,R—DPPACH)(RR—CYDN) and RuHCl(R,R—DPPACH)(RR—DPEN) were prepared as described by Abdur-Rashid et al. (*Organometallics*, 2001, 21, 1047). NMR spectra were recorded on either a Varian Gemini 300 MHz spectrometer (300 MHz for $^1$H, 75 MHz for $^{13}$C and 121.5 for $^{31}$P) or a Varian Unity 400 MHz spectrometer (400 MHz for $^1$H and 100 MHz for $^{13}$C). All $^{31}$P spectra were recorded with proton decoupling and $^{31}$P chemical shifts were measured relative to 85% $H_3PO_4$ as an external reference. $^1$H and $^{13}$C chemical shifts were measured relative to partially deuterated solvent peaks but are reported relative to tetramethylsilane. Infrared spectra were obtained on a Nicolet 550 Magna-IR spectrometer.

Example 1

Preparation of the Ligand R,R—DCYPPACH and Complexes

R,R-1,2-Bis(dicyclohexylphosphinamino)cyclohexane (RR—DCYPPACH): A solution of chlorodicyclohexylphosphine (4.07 g, 17.5 mmol) in toluene (20 ml) was added dropwise to a solution of R,R-1,2-cyclohexyldiamine (1.0 g, 8.75 mmol) and triethylamine (2.0 g, 19.4 mmol) in toluene (20 ml) and the resulting suspension stirred for 6 hours at room temperature. It was then evaporated to dryness, the solids washed with ethanol (2×10 ml) (in order to remove triethylammonium chloride) and hexanes (3×5 ml) and dried under vacuum. Yield=3.86 g, 87%. $^1$H NMR: 0.95-2.38 ppm (m); $^{31}$P{$^1$H} NMR: 51.3 ppm (s).

RuHCl(R,R—DCYPPACH)($PPh_3$): Tetrahydrofuran (10 ml) was added to RuHCl($PPh_3$)$_3$ (1.50 g, 1.63 mmol) and R,R—DCYPPACH (900 mg, 1.77 mmol) and the mixture refluxed for 4 hours under argon. The mixture was filtered and the brick-red solution used as a stock solution, since the product is an oil at room temperature. $^1$H NMR: −16.70 ppm (dt, 1H, RuH, $^2J_{HP}$=35.1, 22.2 Hz), 0.52-3.58 ppm (m, 56H), 7.02-7.39 ppm (m, 15H). $^{31}P\{^1H\}$: 38.21 ppm (br d, $^2J_{PP}$=252 Hz), 110.1 ppm (br d, $^2J_{PP}$=252 Hz), 142 ppm (br s).

RuHCl(R,R—DCYPPACH)(R,R—CYDN): Tetrahydrofuran (2 ml) was added to a mixture of RuHCl(R,R—DCYPPACH)(PPh$_3$) (300 mg, 0.34 mmol) and R,R-cyclohexyldiamine (40 mg, 0.35 mmol) and the resulting solution stirred for 30 minutes under nitrogen. It was then filtered and the solution used as a stock for the complex, which is a pale yellow oil at room temperature. $^1$H NMR: −19.1 ppm (dd, 1H, RuH, $^2J_{HP}$=28.8 Hz, $^2J_{PP}$=42.7 Hz), 0.05-3.54 ppm (m, 56H). $^{31}P\{^1H\}$: 128.5 ppm (d), 108.2 ppm (d), $^2J_{PP}$=42.7 Hz.

Example 2

Preparation of Imines

All imines were prepared by refluxing stoichiometric amounts of the appropriate ketone and amine in toluene or THF over 4 Å molecular sieves until there is no further change in the composition of the mixture with time. The excess ketone and amine are removed under vacuum, and the resulting imine purified by distillation.

Structure of Ligands

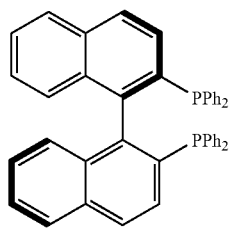

R-BINAP

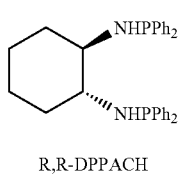

R,R-DPPACH

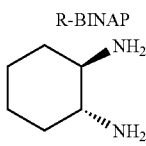

R,R-CYDN

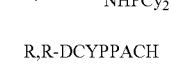

R,R-DCYPPACH

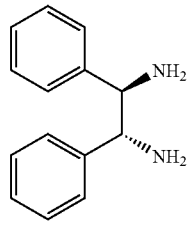

R,R-DPEN

Example 3

Catalytic Hydrogenation

The required substrate was added to a mixture of the catalyst precursor and KO$^i$Pr or KO$^t$Bu in a 250 ml Schlenk flask (benzene or THF was added to dissolve solid imines), which was then cooled to liquid nitrogen temperature. The flask was evacuated under vacuum, filled with H$_2$ gas, closed and allowed to gradually warm to room temperature. The mixture was stirred vigorously until either hydrogenation is complete or no further change in the composition is observed (NMR). A typical procedure for the hydrogenation of N-(1,5-dimethyl-4-hexenylidene)aniline is illustrated below:

A solution of N-(1,5-dimethyl-4-hexenylidene)aniline (2.0 g) in benzene (2 ml) was added under a flow of hydrogen gas to a mixture of RuHCl(R,R—BINAP)(R,R—CYDN) (5 mg) and KO$^i$Pr (5 mg) in a Schlenk flask. The flask was then cooled to liquid nitrogen temperature, filled with H$_2$ gas, closed and allowed to gradually warm to room temperature. The mixture was vigorously stirred for 24 hours. A $^1$H NMR spectrum of the reaction mixture indicated complete conversion of the imine to the amine. Hexane (10 ml) was added to the mixture, which was then eluted (hexane) through a short column of silica gel in order to remove the spent catalyst and KO$^i$Pr. Evaporation of the hexane under reduced pressure resulted in spectroscopically pure N-(1,5-dimethyl-4-hexenyl)aniline, as verified by $^1$H and $^{13}$C NMR.

Proof of principle catalytic hydrogenation results using the series of ruthenium monohydride complexes are summarized below.

(a) Hydrogenation of N-(1-cyclopropylethylidene)aniline

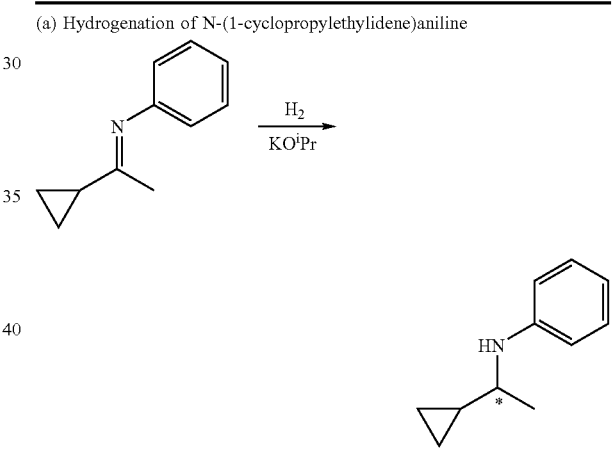

| Catalyst Precursor | S:C | Conversion (%) | Time (hr) |
|---|---|---|---|
| RuHCl(R-BINAP)(R,R-CYDN) | 1700 | 100 | <48 |
| RuHCl(R-BINAP)(R,R-DPEN) | 1700 | 100 | <48 |

(b) Hydrogenation N-(1-cyclobutylethylidene)aniline

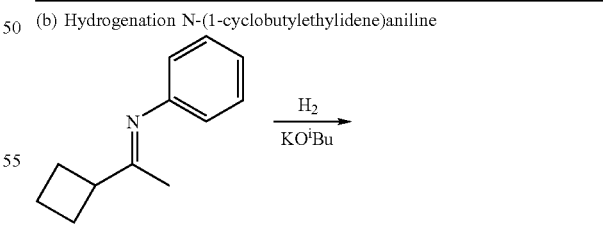

-continued

| Catalyst Precursor | S:C | Conversion (%) | Time (hr) |
|---|---|---|---|
| RuHCl(R-BINAP)(R,R-DPEN) | 1600 | 100 | <30 |

(c) Hydrogenation of N-(1-aza-bicyclo[2.2.2]oct-3-ylidene)aniline

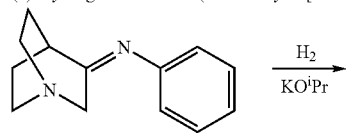

| Catalyst Precursor | S:C | Conversion (%) | Time (hr) |
|---|---|---|---|
| RuHCl(R-BINAP)(R,R-CYDN) | 200 | 100[a] | <12 |
| RuHCl(R-BINAP)(R,R-DPEN) | 500 | 100[b] | <12 |
| RuHCl(R,R-DPPACH)(R,R-CYDN) | 200 | 100 | <12 |
| RuHCl(R,R-DPPACH)(R,R-DPEN) | 200 | 100 | <12 |
| RuHCl(R,R-DCYPPACH)(R,R-CYDN) | 200 | 0 | 12 |

[a]Rotation ($\alpha_D$) = 24.7° (c = 1.0, $CH_2Cl_2$)
[b]Rotation ($\alpha_D$) = 24.2° (c = 1.0, $CH_2Cl_2$)

(d) Hydrogenation of N-(1,2-dimethyl-propylidene)aniline

| Catalyst Precursor | S:C | Conversion (%) | Time (hr) |
|---|---|---|---|
| RuHCl(R-BINAP)(R,R-CYDN) | 600 | 92 | 60 |
| RuHCl(R-BINAP)(R,R-DPEN) | 600 | 95 | 72 |

(e) Hydrogenation of N-(1,5-dimethyl-4-hexenylidene)aniline

| Catalyst Precursor | S:C | Conversion (%) | Time (hr) |
|---|---|---|---|
| RuHCl(R-BINAP)(R,R-CYDN) | 1300 | 100[c] | 48 |
| RuHCl(R-BINAP)(R,R-DPEN) | 1300 | 100[d] | 60 |

[c]Rotation ($\alpha_D$) = 4.60 (c = 1.0, $CH_2Cl_2$)
[d]Rotation ($\alpha_D$) = 4.20 (c = 1.0, $CH_2Cl_2$)

(f) Hydrogenation of N-(1,2-dimethyl-3-phenyl-aliylidene)aniline

| Catalyst Precursor | S:C | Conv. (IV, V %) | Time (hr) e.e. |
|---|---|---|---|
| RuHCl(binap)(cydn) | 200 | 17, 83 | 24 |
| RuHCl(binap)(dpen) | 200 | 22, 78 | 24 |
| RuHCl(dppach)(cydn) | 500 | 34, 66 | 4 |
| RuHCl(dppach)(dpen) | 500 | 75, 25 | 4 |

(g) Hydrogenation of N-(1,2,2-trimethyl-propylidene)aniline

| Catalyst Precursor | S:C | Conversion (%) | Time (hr) |
|---|---|---|---|
| RuHCl(R-BINAP)(R,R-DPEN) | 250 | 5 | 24 |

-continued (h) Hydrogenation of N-(1,2-dimethyl-3-(2-chlorophenyl)-allylidene) aniline

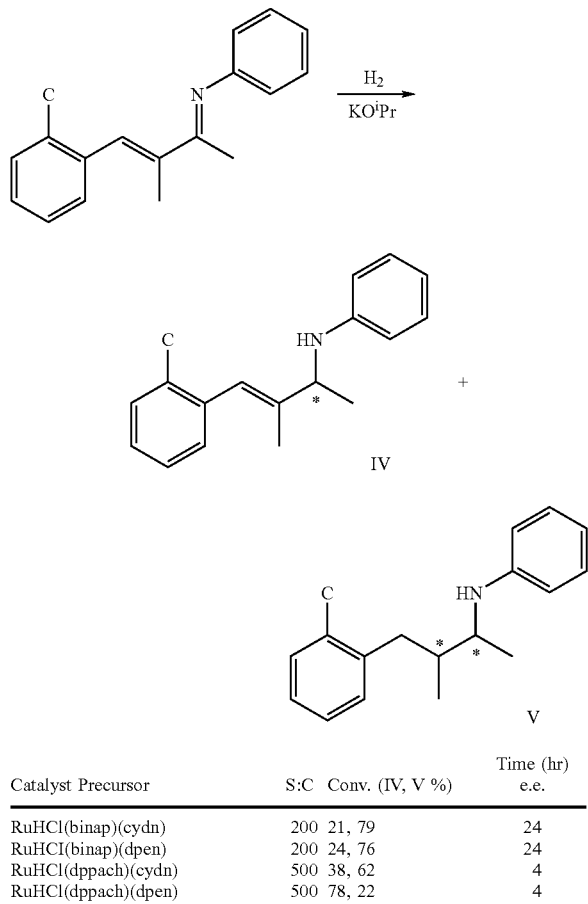

| Catalyst Precursor | S:C | Conv. (IV, V %) | Time (hr) e.e. |
|---|---|---|---|
| RuHCl(binap)(cydn) | 200 | 21, 79 | 24 |
| RuHCl(binap)(dpen) | 200 | 24, 76 | 24 |
| RuHCl(dppach)(cydn) | 500 | 38, 62 | 4 |
| RuHCl(dppach)(dpen) | 500 | 78, 22 | 4 |

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

What is claimed is:

1. A process for the hydrogenation and/or asymmetric hydrogenation of dialkyl, alkylalkenyl or dialkenyl imines of formula II to amines of formula III:

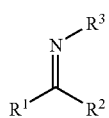
(II)

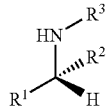
(III)

wherein $R^1$ and $R^2$ are independently selected from the group consisting of optionally substituted cyclic, linear and branched alkyl and alkenyl and wherein $R^1$ and $R^2$ may also be linked together, or with $R^3$, to form one or more rings; and $R^3$ is selected from the group consisting of hydrogen, hydroxy, optionally substituted $C_1$ to $C_8$ cyclic, linear and branched alkyl and alkenyl, and optionally substituted aryl;

said process comprising reacting imines of formula II in the presence of $H_2$ and a catalytic system comprising a base and a ruthenium complex containing (1) a diamine and (2) a diphosphine ligand or monodentate phosphine ligands.

2. A process for preparing enantiomerically enriched chiral dialkyl, alkylalkenyl or dialkenyl amines of formula III, or the opposite enantiomer thereof, from an imine of formula II:

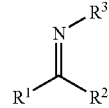
(II)

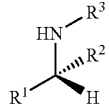
(III)

wherein $R^1$ and $R^2$ are independently selected from the group consisting of optionally substituted cyclic, linear and branched alkyl and alkenyl and wherein $R^1$ and $R^2$ may also be linked together, or with $R^3$, to form one or more rings; and $R^3$ is selected from the group consisting of hydrogen, hydroxy, optionally substituted $C_1$ to $C_8$ cyclic, linear and branched alkyl and alkenyl, and optionally substituted aryl;

said process comprising reacting imines of formula II in the presence of $H_2$ and a catalytic system comprising a base and a ruthenium complex containing (1) a diamine and (2) a chiral diphosphine ligand or chiral monodentate phosphine ligands.

3. The process according to claim 1, wherein said ruthenium complex has the general formula $RuXY(PR_3)_2(NH_2-Z-NH_2)$ (IV) or $RuXY(R_2P-Q-PR_2)(NH_2-Z-NH_2)$ (V), wherein Z and Q represent chiral or achiral linkers, the ancilliary ligands, $PR_3$ and $R_2P-Q-PR_2$, represent chrial or achrial monodentate and bidentate phosphines, respectively and the ligands X and Y represent any anionic ligand.

4. The process according to claim 3, wherein the ligand PR$_3$ (VI):

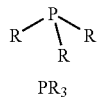

PR$_3$ represents a chiral or achiral monodentate phosphine ligand wherein each R, taken separately, is independently selected from the group consisting of optionally substituted linear and branched alkyl and alkenyl containing 1 to 8 carbon atoms, optionally substituted cycloalkyl, optionally substituted aryl, or OR and NR$_2$, wherein R is as previously defined; or two R groups bonded to the same P atom are bonded together to form an optionally substituted saturated or aromatic ring having 5 to 8 atoms including the phosphorous atom to which said R groups are bonded.

5. The process according to claim 3, wherein the ligand R$_2$P—Q—PR$_2$ (VII):

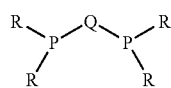

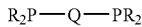

represents a chiral or achiral bidentate ligand wherein each R, taken separately, is independently selected from the group consisting of optionally substituted linear and branched alkyl and alkenyl containing 1 to 8 carbon atoms, optionally substituted cycloalkyl, optionally substituted aryl, or OR and NR$_2$, wherein R is as previously defined; or two R groups bonded to the same P atom are bonded together to form an optionally substituted saturated or aromatic ring having 5 to 8 atoms including the phosphorous atom to which said R groups are bonded; Q is selected from the group consisting of optionally substituted linear and cyclic C$_2$-C$_7$ alkylene, optionally substituted metallocenediyl and optionally substituted C$_6$-C$_{22}$ arylene.

6. The process according to claim 5, wherein the ligand R$_2$P—Q—PR$_2$ (VII) is chiral.

7. The process according to claim 5, wherein the ligand R$_2$P—Q—PR$_2$ (VII) is selected from the group consisting of BINAP, BIPHEP and BIPHEMP.

8. The process according to claim 3, wherein the bidentate phosphine is a chiral or achiral ligand of the formula R$_2$P—NR'—Z—NR'—PR$_2$ (VIII):

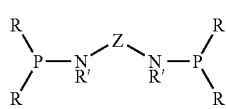

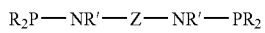

wherein each R, taken separately, is independently selected from the group consisting of optionally substituted linear and branched alkyl and alkenyl containing 1 to 8 carbon atoms, optionally substituted cycloalkyl, optionally substituted aryl, or OR and NR$_2$, wherein R is as previously defined; or two R groups bonded to the same P atom are bonded together to form an optionally substituted saturated or aromatic ring having 5 to 8 atoms including the phosphorous atom to which said R groups are bonded; each R', taken separately, is independently selected from the group consisting of hydrogen, optionally substituted linear and branched alkyl or alkenyl containing 1 to 8 carbon atoms, optionally substituted cycloalkyl and optionally substituted aryl; and Z is selected from the group consisting of optionally substituted linear and cyclic C$_2$-C$_7$ alkylene, optionally substituted metallocenediyl and optionally substituted C$_6$-C$_{22}$ arylene.

9. The process according to claim 8, wherein the ligand R$_2$P—NR'—Z—NR'—PR$_2$ (VIII) is selected from the group consisting of R,R—DPPACH and R,R—DCYPPACH.

10. The process according to claim 1, wherein the diamine ligand has the formula NH$_2$—Z—NH$_2$ (IX):

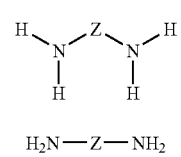

H$_2$N—Z—NH$_2$ wherein Z is selected from the group consisting of optionally substituted linear and cyclic C$_2$-C$_7$ alkylene, optionally substituted metallocenediyl and optionally substituted C$_6$-C$_{22}$ arylene.

11. The process according to claim 10, wherein the diamine ligand is chiral.

12. The process according to claim 10, wherein the diamine ligand NH$_2$—Z—NH$_2$ (IX) is selected from the group consisting of R,R—CYDN and R,R—DPEN.

13. The process according to claim 1, wherein the diamine is a bidentate ligand of the formula D—Z—NHR$_4$ (X), wherein Z is selected from the group consisting of optionally substituted linear and cyclic C$_2$-C$_7$ alkylene, optionally substituted metallocenediyl and optionally substituted C$_6$-C$_{22}$ arylene; D is an amido group donor; and R$^4$ is selected from the group consisting of hydrogen, optionally substituted linear and branched alkyl and alkenyl containing 1 to 8 carbon atoms, optionally substituted cycloalkyl and optionally substituted aryl.

14. The process according to claim 13 wherein D is NR$^5$, wherein R$^5$ is selected from the group consisting of S(O)$_2$R$^6$, P(O)(R$^6$)$_2$, C(O)R$^6$, C(O)N(R$^6$)$_2$ and C(S)N(R$^6$)$_2$ wherein each R$^6$, taken separately, is independently selected from the group consisting of hydrogen, optionally substituted linear and branched alkyl and alkenyl containing 1 to 8 carbon atoms, optionally substituted cycloalkyl and optionally substituted aryl.

15. The process according to claim 13, wherein the diamine is chiral.

16. The process according to claim 3, wherein the ligands X and Y are selected from the group consisting of Cl, Br, I, H, hydroxy, alkoxy or acyloxy.

17. The process according to claim 1, wherein the base is an alcoholate or an hydroxide salt selected from the group consisting of the compounds of formula (R$^7$O)$_2$M' and R$^7$OM", wherein M' is an alkaline-earth metal, M" is an alkaline metal and R$^7$ stands for hydrogen or C$_1$ to C$_6$ linear or branched alkyl.

18. The process according to claim 1, wherein the base is an organic non-coordinating base.

19. The process according to claim 18, wherein the base is selected from the group consisting of DBU, NR$_3$ and phosphazene.

20. The process according to claim 1, wherein the hydrogenation is carried out in the absence of a solvent.

21. The process according to claim 1, wherein the hydrogenation reaction is carried out in the presence of a solvent.

22. The process according to claim 21, wherein the solvent is selected from the group consisting of benzene, toluene, xylene, hexane, cyclohexane, tetrahydrofuran, primary and secondary alcohols, and mixtures thereof.

23. The process according to claim 6, wherein the ligand R2P—Q—PR2 (VII) is selected from atropisomeric bis-tertiary phosphines, in which the two phosphorus atoms are linked by a biaryl backbone.

24. The process according to claim 11 wherein the diamine ligand is selected from (1) compounds in which at least one of the amine-bearing centers is stereogenic, (2) compounds in which both of the amine-bearing centers are stereogenic and (3) atropisomeric bis-tertiary diamines, in which the two nitrogen atoms are linked by a biaryl backbone.

25. The process according to claim 15, wherein the diamine ligand is selected from (1) compounds in which the amine-bearing center is stereogenic, and (2) compounds in which both amido group donor (D)-bearing and amine-bearing centers are stereogenic.

* * * * *